United States Patent [19]

Goel et al.

[11] Patent Number: 4,657,815

[45] Date of Patent: Apr. 14, 1987

[54] SURFACE MODIFICATION OF INORGANIC FILLERS BY TREATMENT WITH BICYCLIC AMIDE ACETALS

[75] Inventors: Anil B. Goel, Worthington; Robert A. Grimm, Columbus; Peggy A. Blackburn, Plain City; Harvey J. Richards, Columbus, all of Ohio

[73] Assignee: Ashland Oil, Inc., Ashland, Ky.

[21] Appl. No.: 858,780

[22] Filed: May 2, 1986

[51] Int. Cl.[4] .......................... B05D 7/00; B32B 5/16; C03C 17/00; C07D 498/00
[52] U.S. Cl. .................................. 428/403; 427/220; 427/255.6; 428/404; 428/406; 428/407; 548/218; 65/60.3

[58] Field of Search .............................. 427/220, 255.6; 428/403, 404, 406, 407; 548/218; 65/60.3

[56] References Cited

U.S. PATENT DOCUMENTS 4,542,066  9/1985  Delzant ........................... 427/220 X
4,558,114 12/1985  Goel ................................ 548/218 X
4,605,746  8/1986  Goel ..................................... 548/218

Primary Examiner—Michael R. Lusignan
Attorney, Agent, or Firm—John F. Jones

[57] ABSTRACT

The process for modifying the surface of a filler or reinforcing material comprising contacting said surface with a bicyclic amide acetal at a temperature in the range of from about 60° C. to about 350° C. is described.

6 Claims, No Drawings

SURFACE MODIFICATION OF INORGANIC FILLERS BY TREATMENT WITH BICYCLIC AMIDE ACETALS

This invention relates to the modification of the surface of fillers and reinforcing materials by treatment with bicyclic amide acetals and to the products of such treatment which have improved properties of compatibility with organic resins.

The use of bicyclic amide acetals as modifiers for the surface of fillers and reinforcing materials such as glass, kaolin, carbon, and the like in order to improve the properties of such fillers such as adhesion (or wetability) to organic resins has not previously been described in the prior art.

We have discovered that surface modified fillers and reinforcement materials have improved compatibility with polymeric resin compositions and that they give reinforced (filled) polymers and composite materials which have improved properties including improved adhesive and cohesive strength. These modified fillers and reinforcement materials may be used in applications such as adhesives, composites, molding compositions, and the like.

Certain fillers and reinforcement fibers are often treated with certain organic and organometallic reagents in order to improve the compatibility of these materials with organic monomers and polymeric resin compositions which result in improvement of the adhesion of the polymeric resins with these fillers and reinforcement materials. The prior art surface modifiers which are sometimes called sizing agents usually serve the purpose of a bridge between the inorganic and the organic materials. For instance, for glass beads and fibers, organosilicon compounds are common sizing agents. These sizing agents may also contain functionalities such as amine, hydroxy, etc. which provide the reactive sites for certain reactive molecules. The untreated fillers and reinforcement materials are often incompatible with organic resins giving poor adhesion and other undesirable properties when incorporated into such resins.

We have found that bicyclic amide acetals may be used as effective surface modification reagents for a variety of fillers and reinforcement materials including glass, kaolin, carbon, and the like. The bicyclic amide acetals useful in this invention include those of Formula I

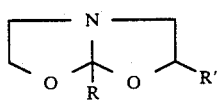

wherein R and R' independently represent hydrogen, an alkyl group having from 1 to 20 carbon atoms, an aryl group having from 6 to 12 carbon atoms, an alkaryl group having from 7 to 20 carbon atoms, an alkyl ether group having from 1 to 20 carbon atoms or an aryl ether group having from 6 to 20 carbon atoms. These bicyclic amide acetals are prepared according to a process disclosed in Ser. No. 641,238, filed Aug. 16, 1984, now U.S. Pat. No. 4,605,746, issued Aug. 12, 1986.

The surface treatment process of this invention may be carried out either in liquid or vapor phase of the bicyclic amide acetal at temperatures ranging from about 60 degrees C. to about 350 degrees C. The fillers may be treated with the vapors of bicyclic amide acetal at high temperatures or with liquid bicyclic amide acetal or its solution in an organic solvent. Because bicyclic amide acetals are highly moisture sensitive, the treatment must be carried out in dry and inert atmosphere. In the course of surface modification of inorganic fillers, it is believed that the bicyclic amide acetal is either chemically bound by interacting with the reactive functionalities of the material or simply adsorbed in or on the material. Because of the highly reactive and polar nature of the bicyclic amide acetal, it serves as a compatibilizer with organic molecules. In addition to this, in some cases, the bicyclic amide acetal removes the undesired moisture adsorbed in the fillers simply by reacting with it, thus improving the processing conditions for systems which are very sensitive to moisture; for instance, urethane polymer formation in the polyisocyanate reactions. The bicyclic amide acetal modified fillers and reinforcement material, when used in polymeric compositions in applications such as structural adhesives, molding compositions, composites, etc. show much improved properties such as adhesive and cohesive strengths.

The fillers and reinforcing agents which can be modified by the process of this invention include glass, carbon, talc, kaolin, graphite, Kevlar and other reinforcement organic polymers such as polyamides including nylons, and polyesters including polyethylene terephthalate.

The invention is further illustrated in the following representative examples.

EXAMPLE 1

Glass microspheres (average size 57 micron) (20 g) were treated with the vapors of 2.23 g of a bicyclic amide acetal of Formula I wherein R is methyl and R' is hydrogen. The bicyclic amide acetal vapors were diluted with nitrogen and passed over the glass microspheres maintained at 200–210 degrees C. during a three hour treatment period. The treated microspheres (Sample A) were dried under reduced pressure to remove any unreacted (or unadsorbed) bicyclic amide acetal. A portion of this was washed with three successive 20 ml portions of isopropyl alcohol followed by three 20 ml portions of acetone and then was dried under reduced pressure (Sample B). Another portion of the treated glass microsphere sample was washed with isopropyl alcohol using a Soxhlet extraction technique (Sample C). All three samples (A, B, and C) were analyzed by ESCA for elemental analysis of the surface. The results are summarized in Table 1 which clearly indicates the presence of nitrogen, an element which was not present in the untreated glass and resulted from the addition of bicyclic amide acetal.

TABLE 1

| Sample | Na | F | O | Ca | N | Si | Al |
|---|---|---|---|---|---|---|---|
| Untreated | 1.8 | 2.3 | 43.2 | 2.4 | 0 | 10.0 | 6.0 |
| A | 1.5 | 1.9 | 33.6 | 2.2 | 5.4 | 8.8 | 7.1 |
| B | 0.9 | 1.9 | 35.6 | 2.8 | 3.3 | 11.3 | 7.5 |
| C | 0.9 | 2.3 | 33.8 | 3.0 | 4.7 | 11.4 | 7.1 |

EXAMPLE 2

In a reactor equipped with a mechanical stirrer, a thermometer with a temperature controller, a reflux condenser and a nitrogen inlet, 300 g of mesitylene, 100 g of the bicyclic amide acetal described in Example 1 and 100 g of untreated glass microspheres were added. The resulting mixture was heated at 162-165 degrees C. for five hours. The glass microspheres were filtered under nitrogen at room temperature and were washed with three 30 ml portions of isopropyl alcohol followed by three 30 ml portions of acetone. The microspheres were dried under reduced pressure and were used as filler in the two-component polyurethane elastomer formulation described below. The polyol component was prepared by mixing 179.2 g of ethylene oxide capped poly(propylene oxide) diol (hydroxy No. 37), 0.66 g of ferric acetyl acetonate, 0.24 g of dibutyltin dilaurate and 2.52 g of piperazine. A part (40 g) of this was filled with 30.8 g of bicyclic amide acetal treated glass microspheres from Example 1 to give component A. The isocyanate prepolymer component B was prepared by heating a mixture of 157.8 g of ethylene oxide capped poly(propylene oxide) diol (hydroxy No. 56) and 74.9 g of liquid methylene bis(phenyl isocyanate) (NCO equivalent weight of 144) at 60-70 degrees C. for 3 hours. The elastomeric polymer was prepared by mixing 33.2 g of polyol component A filled with treated glass microspheres and 15 g of isocyanate prepolymer component B and curing into an approximately 60 mils thick sheet at room temperature. The physical properties such as elongation, tensile strength, and Shore A hardness were determined and compared with that of the system using untreated glass microspheres. The results are given in Table 2.

TABLE 2

| Sample | Average Thickness (Inch) | Tensile (psi) | Elongation 1% | Shore A Hardness |
|---|---|---|---|---|
| Treated Microspheres | 0.062 | 192 | 105 | 54 |
| Untreated Microspheres | 0.064 | 137 | 71 | 54 |

EXAMPLE 3

Kaolin (132 g) was treated with 4 g of the bicyclic amide acetal of Example 1 at 60-80 degrees C. for 2 hours. This treated kaolin filler was then mixed with a polyol composition prepared by mixing 249 g of ethylene oxide capped poly(propylene oxide) triol (molecular weight of 3500), 9.3 g of toluene diisocyanate, 113.4 g of poly(alkylene oxide) tetraol (molecular weight of 450), 0.5 g of ferric acetyl acetonate, 0.2 g of stannous octoate, and 4.8 g of piperazine. The viscosity of the filled component A was determined to be about 4700 cps compared to that of the system prepared by using exactly the same ingredients as above except that untreated kaolin which had a viscosity of about 9000 cps was used. A 30 g portion of the component A prepared by using the treated kaolin was mixed with 30 g of an isocyanate prepolymer obtained by mixing 302.7 g of ethylene oxide capped poly(propylene oxide) diol, 150 g of liquid diglycidyl ether of bisphenol-A (epoxy equivalent weight of 180-190), 704.6 g of liquid methylene bis(phenylisocyanate) (NCO equivalent weight of about 144) and 343 g of dried kaolin filler. The mixed adhesive composition was applied between two 13 inch long and 4 inch wide glass sheets of fiberglass reinforced sheet molding compound having a one inch wide overlap and being approximately 30 mils thick glue line. The adhesive bond was cured at 200 degrees F. for 4 minutes, followed by postcuring at 285 degrees F. for 30 minutes. This adhesive test panel was cut to give twelve one inch wide lap shear test specimens which were pulled on an Instron apparatus. All of the samples showed 100% fiber tear in the range of 400-700 psi.

We claim:

1. The process for modifying the surface of a filler or reinforcing material comprising contacting said surface with a bicyclic amide acetal at a temperature ranging from 60 degrees C. to about 350° C.

2. The process of claim 1 wherein the bicyclic amide acetal is one having the formula

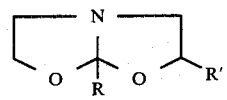

wherein R and R' independently represent hydrogen, an alkyl group having from 1 to 20 carbon atoms, an aryl group having from 6 to 12 carbon atoms, an alkaryl group having from 7 to 20 carbon atoms, an alkyl ether group having from 1 to 20 carbon atoms or an aryl ether group having from 6 to 20 carbon atoms.

3. The process of claim 2 wherein the filler or reinforcing agent is one selected from the group consisting of glass, talc, kaolin, graphite, Kevlar, a polyamide and a polyester.

4. The process of claim 3 wherein the bicyclic amide acetal is one in which R is methyl and R" is hydrogen.

5. The process of claim 4 wherein the filler or reinforcing agent is glass.

6. The product of the process of claim 1.

* * * * *